United States Patent [19]

Eckhardt et al.

[11] Patent Number: 4,528,284
[45] Date of Patent: Jul. 9, 1985

[54] FUNGICIDAL 2-(AZOLYLMETHYL-1'-YL)-2-ARYL-2-(CYANO, ALKOXYCARBONYL, ALKYLTHIOCARBONYL AND AMINOCARBONYL)-2-PHOSPHORUS ACID ESTERS

[75] Inventors: Wolfgang Eckhardt, Lörrach, Fed. Rep. of Germany; Walter Kunz, Oberwil, Switzerland

[73] Assignee: Ciba-Geigy Corporation, Ardsley, N.Y.

[21] Appl. No.: 539,217

[22] Filed: Oct. 5, 1983

[30] Foreign Application Priority Data

Oct. 15, 1982 [CH] Switzerland .................. 6021/82

[51] Int. Cl.³ .................. A01N 57/16; A01N 57/24; C07F 9/65
[52] U.S. Cl. .................. 514/84; 514/85; 514/86; 514/89; 514/93; 514/94; 544/181; 544/182; 544/214; 544/225; 544/226; 544/232; 544/243; 544/337; 546/2; 546/22; 548/101; 548/112
[58] Field of Search .................. 548/101, 112; 546/2, 546/22; 544/181, 182, 214, 225, 232, 226, 243, 337; 424/200

[56] References Cited

FOREIGN PATENT DOCUMENTS 3046309 7/1982 Fed. Rep. of Germany .

Primary Examiner—Richard L. Raymond
Attorney, Agent, or Firm—Edward McC. Roberts; Frederick H. Rabin

[57] ABSTRACT

Phosphoric acid esters of the formula

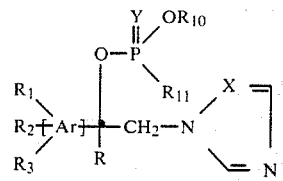

wherein
X is CH or N,
Ar is optionally substituted phenyl, diphenyl or naphthyl,
R is cyano, carboxylic acid ester, carboxylic acid thioester or carboxylic acid amide.
$R_{10}$ is alkyl,
$R_{11}$ alkyl, alkoxy, alkylthio or phenyl, and
Y is sulfur.

For R: the ester groups are alkenyl, alkynyl, cycloalkyl, optionally substituted phenyl, alkyl interrupted by oxygen or sulfur and optionally substituted by halogen, phenyl, carboxylic acid ester, alkylcarbonyl, optionally substituted phenyl carbonyl, or a $C_5$ or $C_6$ heterocycle; the thioester groups are alkyl or optionally substituted phenyl or benzyl; the amide is optionally mono- or di-substituted by alkyl, cycloalkyl, optionally substituted phenyl or benzyl, or may form a $C_5$ or $C_6$ heterocyclic ring. The compounds are useful in controlling phytopathogenic fungi.

11 Claims, No Drawings

FUNGICIDAL 2-(AZOLYLMETHYL-1'-YL)-2-ARYL-2-(CYANO, ALKOXYCARBONYL, ALKYLTHIOCARBONYL AND AMINOCARBONYL)-2-PHOSPHORUS ACID ESTERS

The present invention relates to novel phosphoric acid esters of the formula I below and to the agriculturally acceptable acid addition salts, quaternary azolium and ammonium salts and metal complexes thereof. The invention further relates to the preparation of these compounds as well as to agrochemical pesticidal compositions which contain at least one of the novel compounds as active ingredient. The invention also relates to the preparation of such compositions and to a method of controlling pests or of treating plants to prevent them from attack by pests.

Accordingly, the invention relates to compounds of the formula I

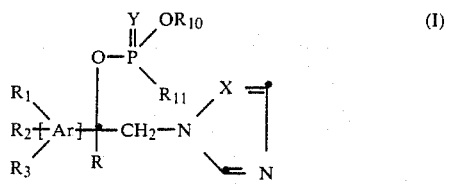

wherein

X is the bridge member —CH= or —N=,

Ar is a phenyl, diphenyl or naphthyl group, $R_1$, $R_2$ and $R_3$ are each independently hydrogen, nitro, halogen, $C_1-C_3$alkyl, $C_1-C_3$alkoxy or $C_1-C_3$haloalkyl, R is one of the groups —$COOR_4$, —$COSR_5$,

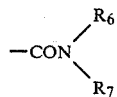

or —CN, $R_4$ is $C_2-C_{10}$alkenyl which is unsubstituted or substituted by halogen: $C_2-C_{10}$alkynyl which is unsubstituted or substituted by halogen; or is a $C_3-C_8$cycloalkyl group or a phenyl group which is unsubstituted or substituted by halogen, $C_1-C_4$alkyl, $C_1-C_4$alkoxy, —CN or —$CF_3$; or is a $C_1-C_{12}$alkyl chain which from $C_2$alkyl may be interrupted by oxygen or sulfur and is unsubstituted or substituted by a member selected from the group consisting of halogen, phenyl, —COO—$C_1-C_4$alkyl, —CO—$C_1-C_4$alkyl, —CO-phenyl, an unsaturated or saturated 5- or 6-membered ring containing oxygen or sulfur as heteroatom, with each phenyl moiety being unsubstituted or substituted by one or more identical or different halogen atoms, $R_5$ is $C_1-C_{10}$alkyl, or is a phenyl or benzyl group, each unsubstituted or, substituted by halogen, $C_1-C_4$alkyl, $C_1-C_4$alkoxy, —CN or —$CF_3$, $R_6$ and $R_7$ are each independently hydrogen, $C_1-C_6$alkyl, $C_3-C_7$cycloalkyl, or a phenyl or benzyl group in each of which the aromatic ring is unsubstituted or substituted by halogen, $C_1-C_4$-alkyl, $C_1-C_4$alkoxy, —CN or —$CF_3$, or one of $R_6$ and $R_7$ is also the —N($R_8$)($R_9$) group, or both taken together form a 5- or 6-membered saturated or unsaturated heterocyclic ring which may additionally contain 1 or 2 further N-atoms, $R_8$ and $R_9$ are each independently hydrogen, $C_1-C_4$alkyl or a phenyl radical which is unsubstituted or substituted by halogen, $C_1-C_4$alkyl, —CN or —$CF_3$, $R_{10}$ is $C_1-C_{12}$alkyl, and $R_{11}$ is —$YR_{12}$, $C_1-C_{12}$alkyl or phenyl, $R_{12}$ is $C_1-C_{12}$alkyl and Y is oxygen or sulfur, and the acid addition salts, quaternary azolium and ammonium salts and the metal complexes thereof.

Depending on the number of indicated carbon atoms, alkyl by itself or as moiety of another substituent comprises e.g. the following groups: methyl, ethyl, propyl, butyl, pentyl, hexyl, heptyl, octyl, nonyl, decyl, undecyl or dodecyl, and the isomers thereof, e.g. isopropyl, isobutyl, tert-butyl, isopentyl etc. Alkenyl is e.g. vinyl, propen-1-yl, allyl, buten-1-yl, buten-2-yl, buten-3-yl etc., as well as chains containing several double bonds. Alkynyl is e.g. propyn-1-yl, propargyl, butyn-1-yl, butyn-2-yl etc., with propargyl being preferred. Haloalkyl is in particular a monohalogenated to perhalogenated alkyl substituent, e.g. $CHCl_2$, $CH_2Cl$, $CCl_3$, $CF_3$, $CH_2CH_2Cl$ etc. Throughout this specification, halogen denotes fluorine, chlorine, bromine or iodine, with chlorine, bromine or fluorine being preferred. Cycloalkyl is e.g. cyclopropyl, cyclobutyl, cyclopentyl, cyclohexyl, or cycloheptyl, with cyclopropyl and cyclohexyl being preferred. Haloalkenyl is an alkenyl group which is substituted by one or more halogen atoms, e.g. chlorine and bromine, preferably chlorine. Furyl is preferably 2-furyl, tetrahydrofuryl, preferably 2-tetrahydrofuryl. Pyridyl is preferably pyrid-3- or -4-yl. Naphthyl is α- or β-naphthyl, preferably α-naphthyl. Examples of heterocyclic 5- or 6-membered rings containing up to 3 nitrogen atoms are pyrazole, imidazole, 1,2,4-triazole and 1,3,4-triazole, pyridine, pyrazine, pyrimidine, pyridazine, 1,3,5-triazine and 1,2,4-triazine.

Examples of salt-forming acids are inorganic acids, e.g. hydrohalic acids such as hydrofluoric acid, hydrochloric acid, hydrobromic acid, or hydriodic acid, and also sulfuric acid, phosphoric acid, phosphorous acid, nitric acid; and organic acids such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid or 2-acetoxybenzoic acid.

Metal complexes of the formula I consist of the basic organic molecule and an inorganic or organic metal salt, for example the halides, nitrates, sulfates, phosphates, acetates, trifluoroacetates, trichloroacetates, propionates, tartrates, sulfonates, salicylates, benzoates etc. of the elements of the third and fourth main group of the Periodic Table such as aluminium, tin or lead, and of the first to eighth auxiliary group such as chromium, manganese, iron, cobalt, nickel, copper, zinc, silver, mercury etc. Preferred elements are those of the auxiliary groups of the fourth period. The metals may exist in different valency states. The metal complexes of the formula I may be monocyclic or polycyclic. i.e. they can contain one or more parts of the organic molecule as ligands. Complexes with copper, zinc, manganese and tin are preferred.

The compounds of formula I are oils, resins or mainly solids which are stable at room temperature and have very valuable microbicidal properties. They can be used in agriculture or related fields preventively and curatively for controlling pests such as fungi, insects and mites, for which utility the triazolylmethyl derivatives falling within the scope of formula I (X is N) are preferred. The compounds of formula I are very well tolerated by cultivated plants. The development of the plants is not impeded or retarded in any stage.

An important and preferred subgroup of compounds of the formula I comprises those of the formula I*

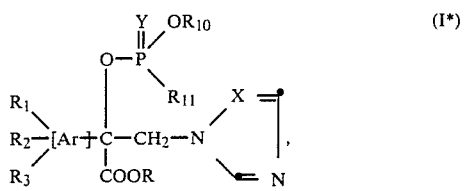 (I*)

wherein
X is the bridge member —CH= or —N=,
Ar is a phenyl, diphenyl or naphthyl group,
$R_1$, $R_2$ and $R_3$ are each independently hydrogen, nitro, halogen, $C_1$-$C_3$alkyl, $C_1$-$C_3$alkoxy or $C_1$-$C_3$haloalkyl,
$R_4$ is $C_1$-$C_4$alkyl, phenyl, or phenyl or benzyl, each substituted by one or more nitro nitro groups, halogen atoms and/or methyl groups,
$R_{10}$ is $C_1$-$C_6$alkyl,
$R_{11}$ is —$YR_{12}$, $C_1$-$C_6$alkyl or phenyl,
$R_{12}$ is $C_1$-$C_6$alkyl, and
Y is oxygen or sulfur,
and the agriculturally suitable acid addition salts, quaternary azolium and ammonium salts and metal complexes thereof.

A further preferred subgroup comprises compounds of formula I, wherein X is the bridge member —CH= or —N=; Ar is a phenyl group; $R_1$ in the ortho-position is hydrogen, nitro, halogen, $C_1$-$C_3$alkyl, $C_1$-$C_3$alkoxy, or $C_1$-$C_3$haloalkyl; $R_2$ in the para-position is hydrogen, nitro, halogen, $C_1$-$C_3$alkyl, $C_1$-$C_3$alkoxy or $C_1$-$C_3$haloalkyl; $R_3$ is hydrogen, methyl or halogen; R is a group —$COOR_4$, —$COSR_5$,

or —CN; $R_4$ is $C_1$-$C_4$alkyl, phenyl, or phenyl or benzyl, each substituted by one or more nitro groups, halogen atoms and/or methyl groups; $R_5$ is $C_1$-$C_{10}$alkyl, or phenyl or benzyl, each unsubstituted or substituted by halogen, $C_1$-$C_4$alkyl, $C_1$-$C_4$alkoxy, —CN or —$CF_3$; each of $R_6$ and $R_7$ independently is hydrogen, $C_1$-$C_3$alkyl, $C_3$-$C_7$cycloalkyl, phenyl or benzyl; $R_{10}$ is $C_1$-$C_4$alkyl; $R_{11}$ is —$YR_{12}$, $C_1$-$C_4$alkyl or phenyl; $R_{12}$ is $C_1$-$C_4$alkyl; and Y is oxygen or sulfur, and the acid addition salts, quaternary azolium and ammonium salts and metal complexes thereof.

This subgroup will be designated throughout as compounds I**.

Yet another particularly preferred subgroup comprises compounds of the formula I, wherein X is the bridge member —N=; the grouping

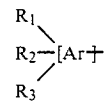

is a phenyl group which is substituted in the ortho- and/or para-position by nitro, fluorine, chlorine, bromine, methyl, methoxy and/or $CF_3$; R is the —$COOR_4$ group; $R_4$ is $C_1$-$C_4$alkyl, phenyl, or phenyl or benzyl, each substituted by nitro, chlorine, bromine, fluorine and/or methyl; $R_{10}$ is $C_1$-$C_4$alkyl; $R_{11}$ is —$YR_{12}$, $C_1$-$C_4$alkyl or phenyl; $R_{12}$ is $C_1$-$C_4$alkyl; and Y is oxygen or sulfur, and the acid addition salts, quaternary azolium and ammonium salts and metal complexes thereof. This subgroup shall be designated throughout as compounds I***.

The following individual compounds are particularly preferred microbicides:

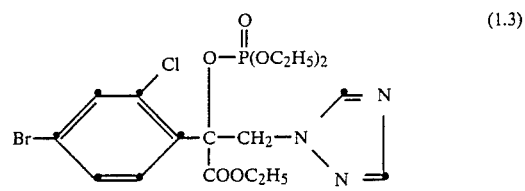 (1.3)

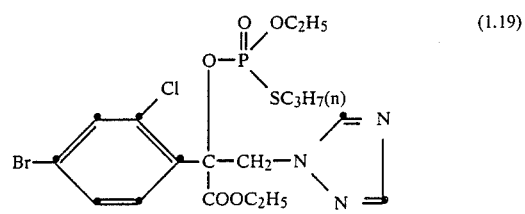 (1.19)

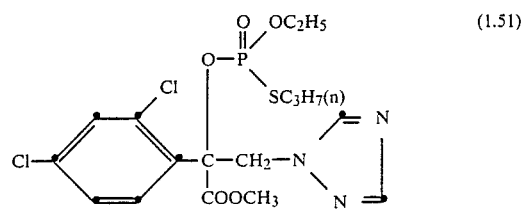 (1.51)

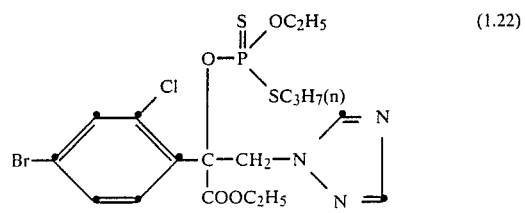 (1.22)

The compounds of formula I are prepared by reacting an alcohol of the formula II

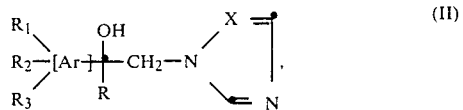 (II)

with a phosphoryl halide of the formula III

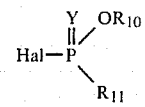
(III)

preferably in the presence of an inorganic or, in particular, of an organic base, in the temperature range from −20° to +150° C., with the preferred range being from 0° to 100° C., and in the absence or preferably in the presence of an inert organic solvent or diluent, and/or converting a free compound obtainable by the process into an acid addition salt or a quaternary azolium or ammonium salt, or converting an acid addition salt or a quaternary azolium or ammonium salt obtainable by the process into the free compound or into another acid addition salt, quaternary azolium or ammonium salt, or converting a free compound or a salt obtainable by the process of the invention into a metal complex. In formulae II and III above, the substituents R, $R_1$, $R_2$, $R_3$, $R_4$, $R_{10}$, $R_{11}$, Y, X and Ar are as defined for formula I, and Hal in formula III is a halogen atom, preferably a chlorine or bromine atom.

Examples of suitable solvents for the reaction are aliphatic and aromatic hydrocarbons such as benzene, toluene, xylenes, petroleum, ether; halogenated hydrocarbons such as chlorobenzene, methylene, chloride, ethylene chloride, chloroform, carbon tetrachloride, tetrachloroethylene; ethers and ethereal compounds such as dialkyl ethers (diethyl ether, diisopropyl ether, tert-butylmethyl ether etc.), anisole, dioxan, tetrahydrofuran; nitriles such as acetonitrile, propionitrile; N,N-dialkylated amides such as dimethylformamide; dimethylsulfoxide; ketones such as acetone, diethyl ketone, methyl ethyl ketone; and mixtures of such solvents with one another. It can often be advantageous to carry out the reaction, or partial steps of a reaction, in an inert gas atmosphere and/or an absolute solvent. Suitable inert gases are e.g. nitrogen, helium, argon or in certain cases, also carbon dioxide. The yield may also be improved by carrying out the reaction under elevated pressure.

Examples of suitable inorganic bases or oxides, hydrides, hydroxides, carbonates, carboxylic acid salts and alcoholates of alkaline earth metals, preferably of alkali metals, in particular those of sodium and potassium (e.g. NaH, NaOH, KOH, $Na_2CO_3$, $K_2CO_3$, $CaCO_3$, $CH_3COONa$, $C_2H_5COOK$, $C_2H_5ONa$, $CH_3ONa$ etc.), preferably the alkali metal hydrides such as NaH. Suitable organic bases are trialkylamines, e.g. triethylamine or other tertiary amines such as triethylenediamine, piperidine, pyridine, 4-dimethylaminopyridine, 4-pyrrolidylpyridine etc.

The intermediates and final products obtained by the preparatory methods of the invention can be isolated from the reaction medium and, if desired, purified by one of the methods conventionally employed, e.g. by extraction, crystallisation, chromatography, distillation etc. Particularly advantageous variants of the process for obtaining the compounds of formula I and for preparing the intermediates, in particular those of formula II, are illustrated in two reaction schemes and subsequently described in detail.

In formulae Ia to Ih, II, III, IV, V, VI, VII, VIII, IX, X, XI, XII, XIII and XIV, the substituents Ar, X, R, $R_1$, $R_2$, $R_3$, $R_4$, $R_5$, $R_6$, $R_7$, $R_8$, $R_9$, $R_{10}$, $R_{11}$ and Y are as defined for formula I.

Q in formula XV is either a customary leaving group, e.g. halogen, preferably chlorine, bromine or iodine, or is a sulfonyloxy group, preferably a benzenesulfonyloxy, p-tosyloxy or lower alkylsulfonyloxy group, preferably a mesyloxy group, or is an acyloxy group such as trifluoroacetyloxy. Q is also a hydroxy group or, according to "Synthesis" 1979, pp. 561–569, is the radical

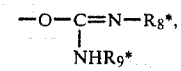

wherein $R_8^*$ and $R_9^*$ are organyl radicals, preferably lower alkyl or unsubstituted or substituted phenyl radicals. M is hydrogen or a metal atom, preferably an alkali metal atom, most preferably sodium or potassium. Hal is halogen, preferably chlorine or bromine. Y is halogen, preferably chlorine or bromine, or is a sulfate or sulfonic acid ester group.

The symbol α denotes the grouping

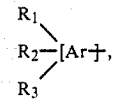

wherein the substituents $R_1$, $R_2$, $R_3$ and Ar are as defined for formula I.

Az denotes the following azolyl group

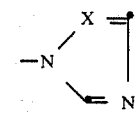

wherein X is —CH= or —N=.

Reaction scheme

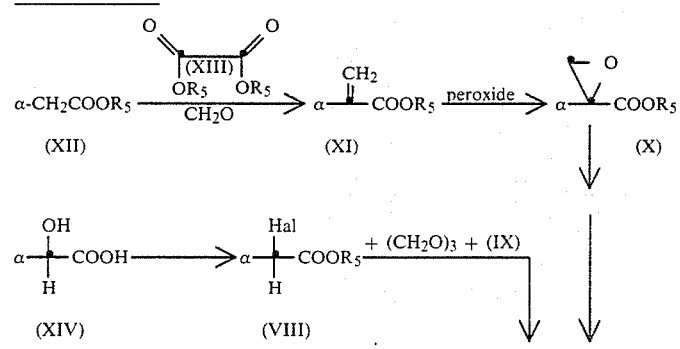

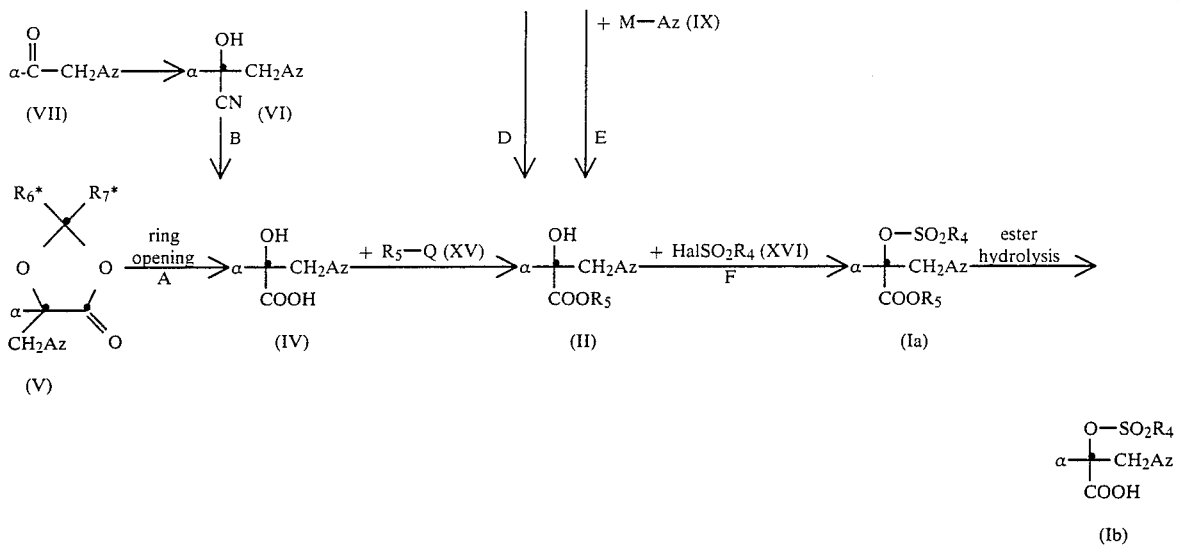

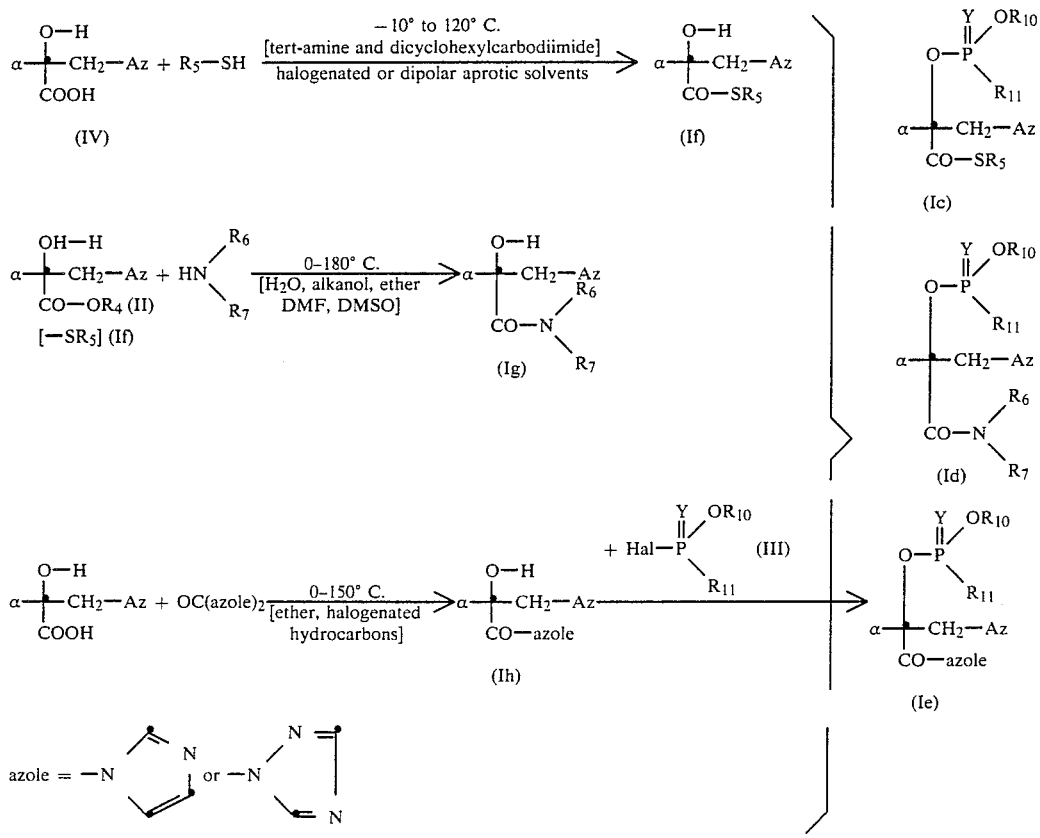

The procedure for preparing the intermediates as well as the compounds of the formula I is, in detail, as follows:

(i) Free α-hydroxycarboxylic acids of the formula IV are prepared by hydrolysing either, according to equation A, a dioxolanone of the formula V or, according to equation B, a cyanohydrin of the formula VI, in basic or acid medium.

The hydrolysis reactions A and B are performed with acids or bases, conveniently in aqueous and/or alcoholic solutions, i.e. in polar solvents. The reactions can also be carried out in two-phase media, which case it is advantageous to add a customary phase-transfer catalyst. Inorganic and organic acids are suitable, e.g. mineral acids such as hydrohalic acids, sulfuric acid, phosphoric acid or sulfonic acids (p-toluenesulfonic acid, methanesulfonic acid). Suitable bases are organic and inorganic bases, e.g. oxides, hydrides, hydroxides, carbonates, carboxylic acid salts and alcoholates of alkaline earth metals and alkali metals, especially those of sodium and potassium.

The reaction temperature for the ring opening reaction A are in general from 0° to +140° C., preferably from +30° to +80° C., and for the hydrolysis of the cyanohydrin III from +60° to +140° C., preferably from +80° to +120° C., or for both reactions at the boiling point of the solvent or solvent mixture.

Most of the starting compounds of the formula V are known from EP Published Specification No. 44276. The novel compounds are prepared by methods corresponding to those described therein.

The nitriles VI (variant B) can be prepared in conventional manner from aryl-azolylmethyl ketones of the formula VII

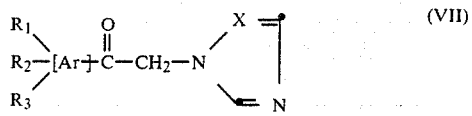

on the lines of a cyanohydrin synthesis, by reaction with HCN or an alkali cyanide, e.g. KCN or NaCN, at 0° to 100° C., advantageously in the presence of a trace of a base (preferably $NH_4OH$ or gaseous ammonia), or by way of the corresponding $NaHSO_3$ adduct VII [Org. Syntheses Coll. Vol. I, p. 336, or French Patent Specification No. 2,292,706; cf. also Houben Weyl "Methoden der organischen Chemie", Vol. 6/3, p. 412].

The nitriles VI can also be prepared in accordance with J. Org. Chem. 39, p. 914 (1974), by reaction of VII with trimethylsilyl cyanide, in the presence of catalytic amounts of $ZnI_2$, and subsequent hydrolysis of the adduct.

These nitriles may also be prepared by reaction of a ketone VII with a di-lower alkylcyanohydrin of the formula

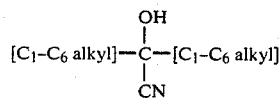

(alkyl is preferably methyl, ethyl or propyl), conveniently in an inert solvent, or without a solvent, at 50°–150° C.

The hydrolysis of the nitriles VI to acid derivatives of the formula IV can be performed by methods similar to known methods, for example with concentrated hydrochloric acid [Houben-Weyl "Methoden der organischen Chemie", Vol. VIII, p. 427 et seq. (1952)].

Some of the ketones of formula VII used as intermediates are known from German Offenlegungsschrift 2 431 407 or from GB Patent Specification No. 1 464 224. Ketones of this type can also be obtained by hydrolysis from corresponding ketals, for example from those which are mentioned in any one of the following publications: German Offenlegungschrift specifications 2 610 022, 2 602 770, 2 930 029, 2 930 196 and 2 940 133.

Ketones of the formula VII which have not been described can be obtained by one of the aforementioned published methods.

(ii) Compounds of the formula II can be prepared according to equation C, in conventional manner, by esterification of the corresponding acid derivative IV (also in the form of its alkali metal salt) with $R_5$-Q (XV) at −20° to +140° C. Aprotic solvents are preferred for this reaction. The direct esterification is advantageously performed with excess alcohol $R_5$-OH at 0° to 80° C. in the presence of a mineral acid, or preferably of a Lewis acid such as boron trifluoride etherate.

Compounds of the formula II can also be prepared according to equation D from an α-haloacetate of the formula VIII with paraformaldehyde at 20° to 140° C., preferably at 40° to 80° C., and (a) with the desired azole of the formula IX (i.e. imidazole or triazole) in the presence of a base (e.g. NaOH), or (b) with an alkali metal salt of the azole of the formula IX in an anhydrous solvent (e.g. dimethylsulfoxide). The α-haloacetates of formula VIII can be obtained by conventional esterification of the known corresponding acids XIV.

Esters of the formula II can also be prepared according to equation E from oxiranes of the formula X with an azole IX (M=H or alkali metal), in an inert, preferably polar, solvent (DMF, acetonitrile, DMSO and others, also in admixture with hydrocarbons), at 20° to 100° C. Inorganic or organic bases can be added in this reaction (cf. also EP Published Specification No. 15756).

As outlined in the reaction scheme, oxiranes of the formula X are obtainable by customary epoxidation (e.g. $H_2O_2$/aqueous NaOH, peracetic acid) from corresponding alkenyl compounds of the formula XI. Compounds of the formula XI are produced from arylacetates of the formula XII by reaction with oxalates of the formula XIII and formaldehyde in the presence of a base [cf. Helvetica Chimica Acta 30, p. 1349 (1947) and German Offenlegungsschrift 2 653 189].

Esters of the formula II can also be prepared from acids of the formula IV and dimethylformamide acetal (preferably in excess), the acetal component of which is intended to form the alcoholic part of the ester, in a solvent (e.g. a similar anhydrous alcohol or an ether) at 0° to 160° C. [Angew. Chemie 75, p. 296 (1963) and Helv. Chim. Acta 48, 1747 (1965)].

(iii) The thioesters of the formula If in the 2nd reaction scheme can be obtained from the acids IV with thioalcohols, in the presence of weak bases (tertiary amines), in aprotic solvents such as $CHCl_3$, DMF, dichloromethane, DMSO, at −10° to +120° C., preferably at 0° to +40° C. These compounds are then reacted with phosphoryl halides of the formula III to give the compounds of the formula Ic. Corresponding mandelic acid amides and mandelic acid hydrazides Ig are obtainable from esters (or thioesters) of the formula If with excess amine $R_7$-NH-$R_8$. The mandelic acid amides and hydrazides Ig are then reacted with compounds of the formula III to give compounds of the formula Id. If $R_6$ and $R_7$ are closed to form a 5- or 6-membered ring, as in the case of compounds of formula Ie, a heterocycle of this kind is introduced avantageously by reaction of the acid IV with 1,1'-carbonyldiazole or -diazine at 0° to 150° C., preferably in a solvent such as an ether or a halogenated hydrocarbon. The resultant compounds of the formula Ih are then reacted with phosphoryl halides of the formula III to give compounds of the formula Ie.

(iv) The free hydroxyl group in compounds IV and II is, as described above, subjected to phosphorylation with phosphoryl halides of the formula III.

All process variants described in (i), (ii), (III) and (iv) constitute an object of the invention.

The other starting compounds of formulae III, IX, XII, XIII and XV are known or they can be obtained by methods which are known per se.

The compounds of formula I

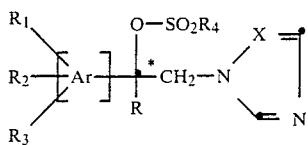

(I)

contain a centre of asymmetry (*) vicinal to the aromatic group Ar and to R, and can therefore be obtained in the form of two enantiomers. In general, a mixture of both enantiomers is obtained in the preparation of these compounds. This mixture can be resolved into the optical antipodes in conventional manner. Optically pure antipodes are obtained e.g. according to variant C by converting an optically pure α-hydroxycarboxylic acid of the formula IV into the optically pure compound of the formula II and phosphorylating it as described in variant F into compounds of the formula Ia, and converting said compounds into further compounds of the formula I by consequent reactions. The optically pure α-hydroxycarboxylic acids of the formula IV can be obtained e.g. via the reaction of racemic acids IV with optically pure bases and fractional crystallisation. Unless otherwise specifically mentioned, reference to a compound of formula I will always be intended to mean a mixture of both enantiomers. Both antipodes have different microbicidal properties.

Surprisingly, it has been found that compounds of the formula I have for practical purposes a very useful microbicidal spectrum against phytopathogenic fungi and bacteria. They have very valuable curative, preventive and systemic properties and can be used for protecting cultivated plants. With the compounds of the formula I it is possible to inhibit or destroy the microorganisms which occur in plants or parts of plants (fruit, blossoms, leaves, stems, tubers, roots) in different crops of useful plants, while at the same time the parts of plants which grow later are also protected from attack by such microorganisms.

The compounds of formula I are effective against the phytopathogenic fungi belonging to the following classes: Ascomycetes (e.g. Venturia, Podosphaera, Erysiphe, Monilinia, Uncinula); Basidomycetes (e.g. the genera Hemileia, Rhizoctonia, Pellicularia, Puccinia); Fungi imperfecti (e.g. Botrytis, Helminthosporium, Fusarium, Septoria, Cercospora, Piricularia and Alternaria) and against Phytomycetes such as Pythium. Compounds of formula I are also effective against phytopathogenic bacteria, in particular against the Xanthomonas species of the Pseudomonadaceae family. In addition, the compounds of formula I have a systemic action. They can also be used as seed dressing agents for protecting seeds (fruits, tubers, grains) and plant cuttings against fungus infections as well as against phytopathogenic microorganisms which occur in the soil. The compounds of the invention are also especially well tolerated by plants. A significant action against rust fungi in cereals and rice varieties merits particular attention.

The compounds of formula I are also suitable for controlling pests of animals and plants and soil pests.

Accordingly, the compounds of formula I are suitable for controlling insects, e.g. of the order Lepidoptera, Coleoptera, Homoptera, Heteroptera, Diptera, Thysanoptera, Orthoptera, Anoplura, Siphonaptera, Mallophaga, Thysanura, Isoptera, Psocoptera and Hymenoptera, as well as phytopathogenic mites and ticks of the order Acarina.

The compounds of formula I control plant-destructive insects, especially plant-destructive insects, especially plant-destructive feeding insects, in ornamentals and crops of useful plants, chiefly in cotton (e.g. against *Spodoptera littoralis* and *Heliothis virescens*) and in vegetables (e.g. against *Leptinotarsa decemlineata* and *Myzus persicae*).

In this connection, it is to be particularly mentioned that the compounds of formula I have both a strongly pronounced systemic and contact action against sucking insects, especially against sucking insects of the order Homoptera and, most particularly, against insects of the Aphididae family (e.g. against *Aphis fabae, Aphis craccivora* and *Myzus persicae*), which can only be controlled with difficulty using known pesticides.

The compounds of formula I also have a very useful action against flies, e.g. *Musca domestica*, and mosquito larvae. In addition, they have a broad ovicidal and ovilarvicidal action. Furthermore, the compounds of formula I have a useful action against ectoparasitic mites and ticks, e.g. of the families Ixodidae, Argasidae and Dermanyssidae.

Accordingly, the invention also relates to microbicidal compositions and to the use of compounds of the formula I for controlling agricultural pests, especially plant-destructive fungi and insects, and for the preventive treatment of plants to protect them from attack by such pests.

The invention further embraces the preparation of agrochemical compositions which comprises homogeneously mixing the active ingredient with one or more compounds or groups of compounds described herein. The invention furthermore relates to a method of treating plants, which comprises applying thereto the compounds of the formula I or the novel compositions.

Target crops to be protected within the scope of the present invention comprise e.g. the following species of plants:

cereals (wheat, barley, rye, oats, rice, sorghum and related crops), beet (sugar beet and fodder beet), drupes, pomes and soft fruit (apples, pears, plums, peaches, almonds, cherries, strawberries, rasberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals.

The compounds of formula I are normally applied in the form of compositions and can be applied to the crop area or plant to be treated, simultaneously or in succession, with other compounds. These other compounds can be both fertilisers or micronutrient donors or other preparations that influence plant growth. They can also be selective herbicides, insecticides, fungicides, bactericides, nematicides, mollusicides or mixtures of several of these compounds, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. Like the nature of the compositions, the methods of application, such as spraying, atomising, dusting, scattering or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 200 g to 600 g a.i./ha. The application of such compositions can be made direct to the plant or parts thereof (foliar application), or to the locus of the plant (soil application), or to the propagation parts, e.g. by seed application.

The formulations, i.e. the compositions or preparations containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters such as ethylene glycol monomethyl ether, ketones such as cyclohexanone, strongly polar solvents such as N-methyl-2-pyrrolidone, dimethylsulfoxide or dimethylformamide, as well as epoxidised vegetable oils or soybean oil; or water.

The solid carriers used e.g. for dusts and dispersible powders, are normally natural mineral fillers such as calcite, talcum, kaolin, montmorillonite or attapulgite, highly dispersed silicic acid or highly dispersed absorbent polymers. Suitable granulated adsorptive carriers are porous types, for example pumice, broken, brick, sepiolite or bentonite; and suitable nonsorbent carriers are e.g. calcite or dolomite. Pulverised plant residues can also be used. Phospholipids can also be used with particular advantage.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

The surfactants customarily employed in the art of formulation are described e.g. in "McCutcheon's Detergents and Emulsifiers Annual", MC Publishing Corp., Ridgewood, New Jersey, 1981, and H. Stache, "Tensid-Taschenbuch", Carl Hanser-Verlag, Munich/Vienna 1981.

The agrochemical compositions usually contain 0.1 to 99%, preferably 0.1 to 95%, of a compound of the formula I, 1 to 99.9%, preferably 99.8 to 5%, of a solid or liquid adjuvant, and 0 to 25%, preferably 0.1 to 25%, of a surfactant.

Whereas commercial products are preferably formulated as concentrates, the end user will normally employ dilute formulations.

The compositions may also contain further ingredients, such as stabilisers, antifoams, viscosity regulators, binders, tackifiers as well as fertilisers or other active ingredients in order to obtain special effects.

The invention is illustrated in more detail by the following nonlimitative Examples, in which parts and percentages are by weight.

PREPARATORY EXAMPLES

Example P1: Preparation of

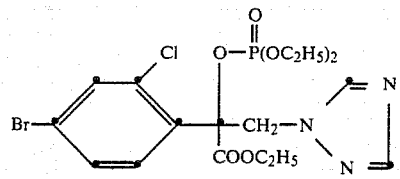

(compound 1.3)

2-(1H-1,2,4-triazolylmethyl-1'-yl)-2-(2-chloro-4-bromophenyl)-2-ethoxycarbonyl-2-phosphoric acid diethyl ester A solution of 15 g (0.04 mole) of diethyl 2-(1H-1,2,4-triazolylmethyl-1'-yl)-2-hydroxy-2-chloro-4-bromophenylacetate in 70 ml of tetrahydrofuran is added dropwise at room temperature to a suspension of 1.8 g (0.04 mole) of a 55% dispersion of sodium hydride in paraffin oil in 50 ml of tetrahydrofuran. Evolution of hydrogen is complete after about 2 hours and then a solution of 8.3 g (0.048 mole) of diethyl chlorophosphate in 70 ml of tetrahydrofuran are added dropwise at room temperature and the reaction mixture is stirred overnight at the same temperature. The mixture is then stirred for another 16 hours at a bath temperature of 80° C. and subsequently cooled to room temperature. The solvent is removed in a water jet vacuum and the residue is taken up in ethyl acetate and the solution is washed with water. The ethyl acetate solution is dried over sodium sulfate, filtered, and the filtrate is concentrated in a water jet vacuum. The crude product is purified by chromatography through a column of silica gel with diethyl ether and increasing increments of ethanol. Yield: 4 g of a yellow oil with a refractive index of $n_D^{36} = 1.5243$.

Example P2: Preparation of

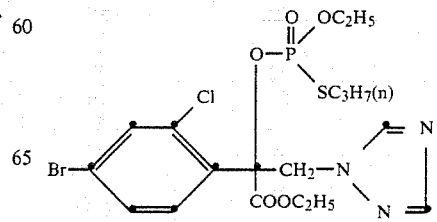

(compound 1.19)

2-(1H-1,2,4-triazolylmethyl-1'-yl)-2-(2-chloro-4-bromophenyl)-2-ethoxycarbonyl-2-phosphoric acid ethyl n-propylthioester A solution of 13.1 g (0.035 mole) of diethyl 2-(1H-1,2,4-triazolylmethyl-1'-yl)-2-hydroxy-2-chloro-4-bromoacetate in 60 ml of tetrahydrofuran is added dropwise at room temperature to a suspension of 1.5 g (0.035 mole) of a 55% dispersion of sodium hydride in paraffin oil. When the evolution of hydrogen has ceased, a solution of 7.8 g (0.038 mole) of the corresponding phosphoric acid ester chloride in 20 ml of tetrahydrofuran is added dropwise at about 10°–15° C. and the reaction mixture is stirred overnight at room temperature. The mixture is concentrated in a water jet vacuum and the residue is dissolved in ethyl acetate. The solution is washed with water, dried over sodium sulfate and concentrated in a water jet vacuum. The paraffin oil is removed by dissolving the residue in acetonitrile and washing the solution with petroleum ether. After separation of both phases in a separating funnel, the acetonitrile is removed in a water jet vacuum. Yield: 10.5 g of an oil with a refractive index of $n_D^{42} = 1.5359$.

Example P3: Preparation of

2-(1H-1,2,4-triazolylmethyl-1'-yl)-2-(2-chloro-4-bromophenyl)-2-ethoxycarbonyl-2-phosphoric acid ethyl n-propyldithioester 0.9 g (0.02 mole) of a 55% dispersion of sodium hydride are added to 20 ml of tetrahydrofuran and then a solution of 7.5 g (0.02 mole) of the corresponding hydroxy compound in 50 ml of tetrahydrofuran is added at room temperature. Evolution of hydrogen has ceased after 2 hours. Then a solution of 4.8 g (0.022 mole) of the corresponding chlorothiophosphate in 10 ml of tetrahydrofuran is added dropwise at 10°–20° C. and the reaction mixture is stirred overnight at room temperature and then concentrated in a water jet vacuum. The residue is taken up in ethyl acetate and the solution is washed with water, dried over sodium sulfate, filtered, and the filtrate is concentrated in a water jet vacuum. The fresh residue is suspended in a small amount of acetonitrile and the suspension is filtered and the filtrate is washed with petroleum ether. Yield: 6.6 g of the title compound with a melting point of 100°–112° C.

The following compounds can be prepared in accordance with the foregoing Examples and the variants described hereinbefore.

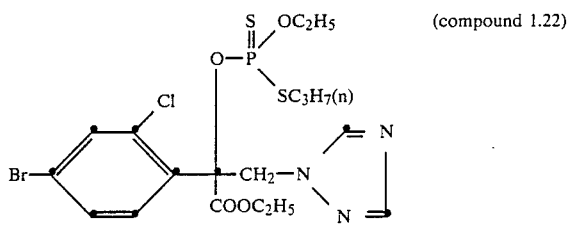

(compound 1.22)

TABLE 1

Compounds of the formula

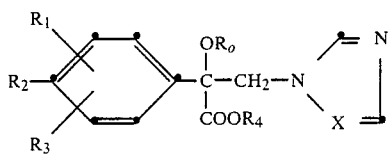

| Compound | R₁, R₂, R₃ | R₀ | R₄ | X | Physical data |
|---|---|---|---|---|---|
| 1.1 | 2-Cl/4-Br | $-P(OC_2H_5)_2$ with =O | $-CH_3$ | N | m.p. 66–74° C. |
| 1.2 | 2-Cl/4-Br | $-P(OC_2H_5)_2$ with =O | $-CH_3$ | CH | |
| 1.3 | 2-Cl/4-Br | $-P(OC_2H_5)_2$ with =O | $-C_2H_5$ | N | $n_D^{36}$: 1.5243 |
| 1.4 | 2-Cl/4-Br | $-P(OC_2H_5)_2$ with =O | $-C_3H_7(n)$ | N | |
| 1.5 | 2-Cl/4-Br | $-P(OC_2H_5)_2$ with =O | $-C_4H_9(n)$ | N | |
| 1.6 | 2-Cl/4-Br | $-P(OC_2H_5)_2$ with =O | cyclohexyl | N | |

TABLE 1-continued

Compounds of the formula

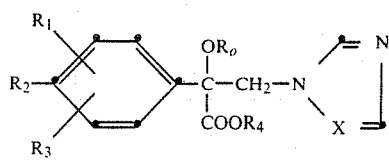

| Compound | $R_1, R_2, R_3$ | $R_o$ | $R_4$ | X | Physical data |
|---|---|---|---|---|---|
| 1.7 | 2-Cl/4-Br | $-\overset{O}{\underset{\|}{P}}(OC_2H_5)_2$ | $-C_6H_5$ | N | |
| 1.8 | 2-Cl/4-Br | $-\overset{O}{\underset{\|}{P}}(OC_2H_5)_2$ | $-CH_2C_6H_5$ | N | |
| 1.9 | 2-Cl/4-Br | $-\overset{O}{\underset{\|}{P}}(OC_2H_5)_2$ | $-CH_2CH_2Cl$ | N | |
| 1.10 | 2-Cl/4-Br | $-\overset{O}{\underset{\|}{P}}(OC_2H_5)_2$ | $-CH_2CH_2OCH_3$ | N | |
| 1.11 | 2-Cl/4-Br | $-\overset{O}{\underset{\|}{P}}(OC_2H_5)_2$ | $-CH_2OCH_3$ | N | |
| 1.12 | 2-Cl/4-Br | $-\overset{O}{\underset{\|}{P}}(OC_2H_5)_2$ | $-CH_2SCH_3$ | N | |
| 1.13 | 2-Cl/4-Br | $-\overset{O}{\underset{\|}{P}}(OC_2H_5)_2$ | $-CH_2CH=CH_2$ | N | |
| 1.14 | 2-Cl/4-Br | $-\overset{O}{\underset{\|}{P}}(OC_2H_5)_2$ | $-CH_2COOC_2H_5$ | N | |
| 1.15 | 2-Cl/4-Br | $-\overset{O}{\underset{\|}{P}}(OC_2H_5)_2$ | $-CH_2COC_4H_9(+)$ | N | |
| 1.16 | 2-Cl/4-Br | $-P\overset{O}{\underset{\|}{\diagup}}\overset{OC_2H_5}{\diagdown}_{SC_4H_9(s)}$ | $-C_2H_5$ | N | |
| 1.17 | 2-Cl/4-Br | $-P\overset{O}{\underset{\|}{\diagup}}\overset{OC_2H_5}{\diagdown}_{SC_3H_7(n)}$ | $-CH_3$ | N | |
| 1.18 | 2-Cl/4-Br | $-P\overset{O}{\underset{\|}{\diagup}}\overset{OC_2H_5}{\diagdown}_{SC_3H_7(n)}$ | $-C_3H_7(i)$ | N | |
| 1.19 | 2-Cl/4-Br | $-P\overset{O}{\underset{\|}{\diagup}}\overset{OC_2H_5}{\diagdown}_{SC_3H_7(n)}$ | $-C_2H_5$ | N | $n_D^{42}: 1,5359$ |
| 1.20 | 2-Cl/4-Br | $-\overset{O}{\underset{\|}{P}}(OCH_3)_2$ | $-C_2H_5$ | N | |
| 1.21 | 2-Cl/4-Br | $-\overset{O}{\underset{\|}{P}}(OC_2H_5)_2$ | $-C_2H_5$ | N | |

TABLE 1-continued

Compounds of the formula

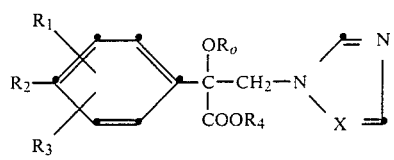

| Compound | $R_1, R_2, R_3$ | $R_o$ | $R_4$ | X | Physical data |
|---|---|---|---|---|---|
| 1.22 | 2-Cl/4-Br | $-P(=S)(OC_2H_5)(SC_3H_7(n))$ | $-C_2H_5$ | N | m.p. 100–112°C. |
| 1.23 | 2-Cl/4-Br | $-P(=O)(OCH_3)(CH_3)$ | $-C_2H_5$ | N | |
| 1.24 | 2-Cl/4-Br | $-P(=O)(OC_2H_5)(C_6H_5)$ | $-C_2H_5$ | N | |
| 1.25 | 4-Cl | $-P(=O)(OC_2H_5)_2$ | $-C_2H_5$ | N | |
| 1.26 | 3-Cl/4-Cl | $-P(=O)(OC_2H_5)_2$ | $-C_2H_5$ | N | |
| 1.27 | 4-F | $-P(=O)(OC_2H_5)_2$ | $-CH_3$ | N | |
| 1.28 | 2-CH$_3$/5-CH$_3$ | $-P(=O)(OC_2H_5)_2$ | $-CH_3$ | N | |
| 1.29 | 2-Cl/4-Cl | $-P(=O)(OC_2H_5)_2$ | $-CH_3$ | N | m.p. 75–78° C. |
| 1.30 | 2-Cl/4-Cl | $-P(=O)(OC_2H_5)_2$ | $-CH_3$ | CH | |
| 1.31 | 2-Cl/4-Cl | $-P(=O)(OC_2H_5)_2$ | $-C_2H_5$ | N | |
| 1.32 | 2-Cl/4-Cl | $-P(=O)(OC_2H_5)_2$ | $-C_3H_7(n)$ | N | |
| 1.33 | 2-Cl/4-Cl | $-P(=O)(OC_2H_5)_2$ | $-C_4H_9(n)$ | N | |
| 1.34 | 2-Cl/4-Cl | $-P(=O)(OC_2H_5)_2$ | $-C_3H_7(i)$ | N | |
| 1.35 | 2-Cl/4-Cl | $-P(=O)(OC_2H_5)_2$ | $-C_4H_9(t)$ | N | |
| 1.36 | 2-Cl/4-Cl | $-P(=O)(OC_2H_5)_2$ | cyclohexyl | N | |
| 1.37 | 2-Cl/4-Cl | $-P(=O)(OC_2H_5)_2$ | $-C_6H_5$ | N | |

TABLE 1-continued

Compounds of the formula

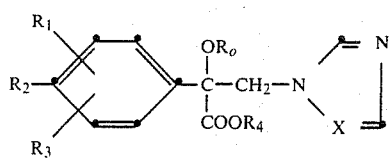

| Compound | $R_1, R_2, R_3$ | $R_o$ | $R_4$ | X | Physical data |
|---|---|---|---|---|---|
| 1.38 | 2-Cl/4-Cl | $-P(O)(OC_2H_5)_2$ | $-CH_2C_6H_5$ | N | |
| 1.39 | 2-Cl/4-Cl | $-P(O)(OC_2H_5)_2$ | $-CH_2CH_2Cl$ | N | |
| 1.40 | 2-Cl/4-Cl | $-P(O)(OC_2H_5)_2$ | $-CH_2CH_2OCH_3$ | N | |
| 1.41 | 2-Cl/4-Cl | $-P(O)(OC_2H_5)_2$ | $-CH_2OCH_3$ | N | |
| 1.42 | 2-Cl/4-Cl | $-P(O)(OC_2H_5)_2$ | $-CH_2SCH_3$ | N | |
| 1.43 | 2-Cl/4-Cl | $-P(O)(OC_2H_5)_2$ | $-CH_2CH=CH_2$ | N | |
| 1.44 | 2-Cl/4-Cl | $-P(O)(OC_2H_5)_2$ | $-CH(CH_3)COOCH_3$ | N | |
| 1.45 | 2-Cl/4-Cl | $-P(O)(OC_2H_5)_2$ | $-CH_2COC_4H_9(t)$ | N | |
| 1.46 | 2-Cl/4-Cl | $-P(O)(OCH_3)_2$ | $-CH_3$ | N | resin |
| 1.47 | 2-Cl/4-Cl | $-P(O)(OC_2H_5)(SC_4H_9(s))$ | $-CH_3$ | N | |
| 1.48 | 2-Cl/4-Cl | $-P(O)(OC_2H_5)(SC_3H_7(n))$ | $-C_2H_5$ | N | |
| 1.49 | 2-Cl/4-Cl | $-P(O)(OC_2H_5)(SC_3H_7(n))$ | $-C_3H_7(n)$ | N | |
| 1.50 | 2-Cl/4-Cl | $-P(O)(OC_2H_5)(SC_3H_7(n))$ | $-CH_2CH=CH_2$ | N | |
| 1.51 | 2-Cl/4-Cl | $-P(O)(OC_2H_5)(SC_3H_7(n))$ | $-CH_3$ | N | resin |
| 1.52 | 2-Cl/4-Cl | $-P(O)(OCH_3)(CH_3)$ | $-CH_3$ | N | |

TABLE 1-continued

Compounds of the formula

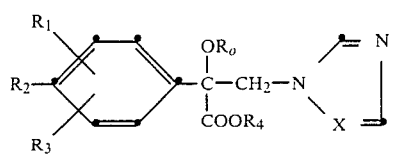

| Compound | $R_1, R_2, R_3$ | $R_o$ | $R_4$ | X | Physical data |
|---|---|---|---|---|---|
| 1.53 | 2-Cl/4-Cl | $-P(=O)(OC_2H_5)(C_6H_5)$ | $-CH_3$ | N | |
| 1.54 | 2-Cl/4-Cl | $-P(=S)(OC_2H_5)_2$ | $-CH_3$ | N | |
| 1.55 | 2-Cl/4-Cl | $-P(=S)(OC_2H_5)(SC_3H_7(n))$ | $-CH_3$ | N | resin |
| 1.56 | 2-Cl/4-Cl | $-P(=S)(OC_2H_5)(SC_3H_7(n))$ | $-C_2H_5$ | N | |
| 1.57 | 2-Cl/4-F | $-P(=O)(OC_2H_5)_2$ | $-CH_3$ | N | |
| 1.58 | 2-Cl/4-F | $-P(=O)(OC_2H_5)(SC_4H_9(s))$ | $-CH_3$ | N | |
| 1.59 | 2-Cl/4-F | $-P(=S)(OC_2H_5)(SC_4H_9(s))$ | $-CH_3$ | N | |
| 1.60 | 2-Cl/4-F | $-P(=O)(OCH_3)(CH_3)$ | $-CH_3$ | N | |
| 1.61 | 2-Cl/4-F | $-P(=O)(OC_2H_5)(C_6H_5)$ | $-CH_3$ | N | |
| 1.62 | 2-Cl/4-F | $-P(=S)(OC_2H_5)(SC_4H_9(s))$ | $-CH_3$ | N | |
| 1.63 | 2-Cl/4-F | $-P(=S)(OC_2H_5)(SC_3H_7(n))$ | $-CH_3$ | N | |
| 1.64 | 2-Cl/4-F | $-P(=O)(OC_2H_5)(SC_3H_7(n))$ | $-CH_3$ | N | |
| 1.65 | 2-Br/4-Br | $-P(=O)(OC_2H_5)_2$ | $-C_2H_5$ | N | resin |

TABLE 1-continued

Compounds of the formula

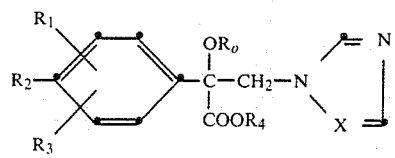

| Compound | $R_1, R_2, R_3$ | $R_o$ | $R_4$ | X | Physical data |
|---|---|---|---|---|---|
| 1.66 | 2-Br/4-Br | $-P(=O)(OC_2H_5)(SC_4H_9(s))$ | $-C_2H_5$ | N | |
| 1.67 | 2-Br/4-Br | $-P(=S)(OC_2H_5)(SC_3H_7(n))$ | $-C_2H_5$ | N | |
| 1.68 | 2-Br/4-Br | $-P(=S)(OC_2H_5)(SC_3H_7-n)$ | $-C_3H_7-i$ | N | m.p. 113–115° C. |

TABLE 2

Compounds of the formula

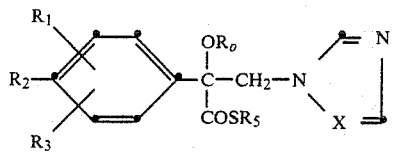

| Compound | $R_1, R_2, R_3$ | $R_o$ | $R_5$ | X | Physical data |
|---|---|---|---|---|---|
| 2.1 | 2-Cl/4-Cl | $-P(=O)(OC_2H_5)$ | $-CH_3$ | N | resin |
| 2.2 | 2-Cl/4-Cl | $-P(=O)(OC_2H_5)$ | $-C_2H_5$ | N | |
| 2.3 | 2-Cl/4-Cl | $-P(=O)(OC_2H_5)$ | $-C_2H_5$ | CH | |
| 2.4 | 2-Cl/4-Cl | $-P(=O)(OC_2H_5)$ | $-C_6H_5$ | N | |
| 2.5 | 2-Cl/4-Cl | $-P(=O)(OC_2H_5)$ | $-CH_2-C_6H_5$ | N | |
| 2.6 | 2-Cl/4-Cl | $-P(=O)(OC_2H_5)$ | $-CH_2CH=CH_2$ | N | |
| 2.7 | 2-Cl/4-Cl | $-P(=O)(OC_2H_5)$ | $-C_4H_9(n)$ | N | |
| 2.8 | 2-Cl/4-Cl | $-P(=O)(OC_2H_5)(SC_3H_7(n))$ | $-C_2H_5$ | N | |

TABLE 2-continued

Compounds of the formula

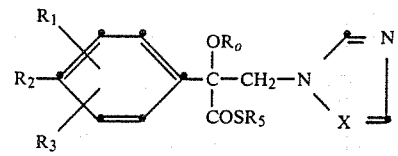

| Compound | $R_1, R_2, R_3$ | $R_o$ | $R_5$ | X | Physical data |
|---|---|---|---|---|---|
| 2.9 | 2-Cl/4-Cl | $-P(=O)(OC_2H_5)(SC_3H_7(n))$ | $-CH_2CH=CH_2$ | N | |
| 2.10 | 2-Cl/4-Cl | $-P(=S)(OC_2H_5)_2$ | $-C_2H_5$ | N | |
| 2.11 | 2-Cl/4-Cl | $-P(=S)(OC_2H_5)(SC_3H_7(n))$ | $-C_2H_5$ | N | |
| 2.12 | 2-Cl/4-Cl | $-P(=O)(OCH_3)(CH_3)$ | $-C_2H_5$ | N | |
| 2.13 | 2-Cl/4-Cl | $-P(=O)(OCH_3)_2$ | $-C_2H_5$ | N | |
| 2.14 | 2-Cl/4-Br | $-P(=O)(OCH_3)_2$ | $-C_2H_5$ | N | |
| 2.15 | 2-Cl/4-Br | $-P(=O)(OC_2H_5)_2$ | $-C_2H_5$ | N | |
| 2.16 | 2-Cl/4-Br | $-P(=O)(OC_2H_5)_2$ | $-C_3H_7(n)$ | N | |

TABLE 2-continued

Compounds of the formula $$\text{R}_1, \text{R}_2, \text{R}_3\text{-phenyl-C}(\text{OR}_o)(\text{COSR}_5)\text{-CH}_2\text{-N(azole, X)}$$

| Compound | $R_1, R_2, R_3$ | $R_o$ | $R_5$ | X | Physical data |
|---|---|---|---|---|---|
| 2.17 | 2-Cl/4-Br | $-\overset{O}{\underset{\|}{P}}(OC_2H_5)(SC_3H_7(n))$ | $-C_2H_5$ | N | |
| 2.18 | 2-Cl/4-Br | $-\overset{S}{\underset{\|}{P}}(OC_2H_5)_2$ | $-C_2H_5$ | N | resin |
| 2.19 | 2-Cl/4-Br | $-\overset{S}{\underset{\|}{P}}(OC_2H_5)(SC_3H_7(n))$ | $-C_2H_5$ | N | |
| 2.20 | 2-Cl/4-Br | $-\overset{O}{\underset{\|}{P}}(OCH_3)(CH_3)$ | $-C_2H_5$ | N | |
| 2.21 | 2-Cl/4-F | $-\overset{O}{\underset{\|}{P}}(OC_2H_5)_2$ | $-C_2H_5$ | N | |
| 2.22 | 2-Cl/4-F | $-\overset{S}{\underset{\|}{P}}(OC_2H_5)(SC_3H_7(n))$ | $-C_2H_5$ | N | |
| 2.23 | 2-Cl/4-F | $-\overset{O}{\underset{\|}{P}}(OCH_3)(CH_3)$ | $-C_2H_5$ | N | |
| 2.24 | 2-Cl/4-F | $-\overset{O}{\underset{\|}{P}}(OC_2H_5)(SC_3H_7)$ | $-C_2H_5$ | N | |

TABLE 3

Compounds of the formula $$\text{R}_1, \text{R}_2, \text{R}_3\text{-phenyl-C}(\text{OR}_o)(\text{CON}R_6R_7)\text{-CH}_2\text{-N(azole, X)}$$

| Compound | $R_1, R_2, R_3$ | $R_o$ | $-NR_6R_7$ | X | Physical data |
|---|---|---|---|---|---|
| 3.1 | 2-Cl/4-Cl | $-\overset{O}{\underset{\|}{P}}(OC_2H_5)_2$ | $-NHCH_3$ | N | |
| 3.2 | 2-Cl/4-Cl | $-\overset{O}{\underset{\|}{P}}(OC_2H_5)_2$ | $-NHCH_3$ | CH | |
| 3.3 | 2-Cl/4-Cl | $-\overset{O}{\underset{\|}{P}}(OC_2H_5)_2$ | $-NHC_2H_5$ | N | |
| 3.4 | 2-Cl/4-Cl | $-\overset{O}{\underset{\|}{P}}(OC_2H_5)_2$ | $-NHCH_2C_6H_5$ | N | |
| 3.5 | 2-Cl/4-Cl | $-\overset{O}{\underset{\|}{P}}(OC_2H_5)_2$ | $-N(C_2H_5)_2$ | N | |
| 3.6 | 2-Cl/4-Cl | $-\overset{O}{\underset{\|}{P}}(CO_2H_5)_2$ | $-NHN(CH_3)_2$ | N | |
| 3.7 | 2-Cl/4-Cl | $-\overset{O}{\underset{\|}{P}}(OC_2H_5)_2$ | $-NHNH_2$ | N | |
| 3.8 | 2-Cl/4-Cl | $-\overset{O}{\underset{\|}{P}}(OC_2H_5)_2$ | -N(imidazolyl) | N | |
| 3.9 | 2-Cl/4-Cl | $-\overset{O}{\underset{\|}{P}}(OC_2H_5)(SC_3H_7(n))$ | $-NHCH_3$ | N | |
| 3.10 | 2-Cl/4-Cl | $-\overset{S}{\underset{\|}{P}}(OC_2H_5)(SC_3H_7(n))$ | $-NHCH_3$ | N | |
| 3.11 | 2-Cl/4-Cl | $-\overset{S}{\underset{\|}{P}}(OC_2H_5)(SC_4H_9(s))$ | $-NHCH_3$ | N | |
| 3.12 | 2-Cl/4-Cl | $-\overset{O}{\underset{\|}{P}}(OCH_3)(CH_3)$ | $-NHCH_3$ | N | |
| 3.13 | 2-Cl/4-Cl | $-\overset{S}{\underset{\|}{P}}(OCH_3)_2$ | $-NHCH_3$ | N | |
| 3.14 | 2-Cl/4-Br | $-\overset{O}{\underset{\|}{P}}(OC_2H_5)_2$ | $-NHCH_3$ | N | |

TABLE 3-continued

Compounds of the formula

| Compound | $R_1, R_2, R_3$ | $R_o$ | $-N\begin{smallmatrix}R_6\\R_7\end{smallmatrix}$ | X | Physical data |
|---|---|---|---|---|---|
| 3.15 | 2-Cl/4-Br | $-P(=O)(OC_2H_5)_2$ | $-NHN(CH_3)_2$ | N | |
| 3.16 | 2-Cl/4-Br | $-P(=S)(OC_2H_5)_2$ | $-NHCH_3$ | N | |
| 3.17 | 2-Cl/4-Br | $-P(=O)(OC_2H_5)(SC_3H_7(n))$ | $-NHCH_3$ | N | |
| 3.18 | 2-Cl/4-Br | $-P(=S)(OC_2H_5)(SC_4H_9(s))$ | $-NHCH_3$ | N | |
| 3.19 | 2-Cl/4-F | $-P(=O)(OC_2H_5)_2$ | $-NHCH_3$ | N | |
| 3.20 | 2-Cl/4-F | $-P(=S)(OCH_3)_2$ | $-NHCH_3$ | N | |
| 3.21 | 2-Cl/4-F | $-P(=O)(OC_2H_5)(SC_4H_9(s))$ | $-NHCH_3$ | N | |
| 3.22 | 2-Cl/4-F | $-P(=O)(OCH_3)(CH_3)$ | $-NHCH_3$ | N | |
| 3.23 | 2-Br/4-Br | $-P(=O)(OC_2H_5)_2$ | $-NHCH_3$ | N | |
| 3.24 | 2-Br/4-Br | $-P(=S)(OC_2H_5)(SC_3H_7(n))$ | $-NHCH_3$ | N | |

TABLE 4

Compounds of the formula

| Compound | Ar | $R_1, R_2, R_3$ | $R_o$ | R | X | Physical data |
|---|---|---|---|---|---|---|
| 4.1 | biphenyl | H | $-P(=O)(OC_2H_5)_2$ | $-COOCH_3$ | N | |
| 4.2 | biphenyl | H | $-P(=S)(OC_2H_5)(SC_3H_7(n))$ | $-COOCH_3$ | N | |
| 4.3 | biphenyl | 4-Cl | $-P(=S)(OC_2H_5)(SC_3H_7(n))$ | $-COOCH_3$ | N | |
| 4.4 | naphthyl | H | $-P(=S)(OC_2H_5)(SC_3H_7(n))$ | $-COOCH_3$ | N | |

TABLE 4-continued

Compounds of the formula

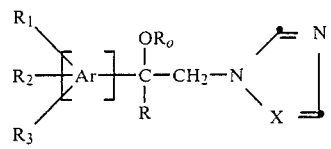

| Compound | Ar | R₁, R₂, R₃ | R₀ | R | X | Physical data |
|---|---|---|---|---|---|---|
| 4.5 | (benzene) | H | $-\overset{O}{\underset{\|}{P}}(OC_2H_5)_2$ | —COOCH₃ | N | |
| 4.6 | (benzene) | 2-CH₃ | $-\overset{O}{\underset{\|}{P}}(OC_2H_5)_2$ | —COOCH₃ | N | |
| 4.7 | (naphthalene) | H | $-\overset{O}{\underset{\|}{P}}(OC_2H_5)_2$ | —COOCH₃ | N | |
| 4.8 | (naphthalene) | H | $-\overset{S}{\underset{\|}{P}}\overset{OC_2H_5}{\underset{SC_3H_7(n)}{}}$ | —COOCH₃ | N | |

Formulation Examples

Formulation Examples for active ingredients of the formula I (throughout, percentages are by weight)

| (A) Emulsifiable concentrates | (a) | (b) | (c) |
|---|---|---|---|
| a compound of Tables 1 to 4 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| (B) Solutions | (a) | (b) | (c) | (d) |
|---|---|---|---|---|
| a compound of Tables 1 to 4 | 80% | 10% | 5% | 95% |
| ethylene glycol monomethyl ether | 20% | — | — | — |
| polyethylene glycol 400 | — | 70% | — | — |
| N—methyl-2-pyrrolidone | — | 20 | — | — |
| epoxidised coconut oil | — | — | 1% | 5% |
| petroleum distillate (boiling range 160-190°) | — | — | 94% | — |

These solutions are suitable for application in the form of microdrops.

| (C) Granulates | (a) | (b) |
|---|---|---|
| a compound of Tables 1 to 4 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| (D) Dusts | (a) | (b) |
|---|---|---|
| a compound of Tables 1 to 4 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| (E) Wettable powders | (a) | (b) | (c) |
|---|---|---|---|
| a compound of Tables 1 to 4 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixtures is thoroughly ground in a suitable mill, affording wettable powders which can be diluted with water to give suspensions of the desired concentration.

BIOLOGICAL EXAMPLES

I. Action against phytopathogenic fungi (a) Residual-protective action

Wheat plants are treated 6 days after sowing with a spray mixture prepared from a wettable powder formulation of the active ingredient (0.06%). After 24 hours the treated plants are infected with a uredospore suspension of the fungus. The infected plants are incubated for 48 hours at 95–100% relative humidity and about 20° C. and then stood in a greenhouse at about 22° C. Evaluation of rust pustule development is made 12 days after infection.

(b) Systemic action

Wheat plants are treated 5 days after sowing with a spray mixture prepared from a wettable powder formulation of the active ingredient (0.006% based on the volume of the soil). After 48 hours the treated plants are infected with a uredospore suspension of the fungus. The plants are then incubated for 48 hours at 95–100% relative humidity and about 20° C. and then stood in a greenhouse at about 22° C. Evaluation of rust pustule development is made 12 days after infection. Attack on untreated and infected control plants is 100%. Plants treated with compositions containing compounds of formula I exhibit only insignificant (<20%) or no attack. Compounds 1.1, 1.3, 1.19, 1.22, 1.65 and others inhibit fungus attack completely (0 to 5%). Compound 1.3 still inhibits fungus attack even when used in a concentration of 0.002%.

EXAMPLE B2: ACTION AGAINST CERCOSPORA ARACHIDICOLA IN GROUNDNUT PLANTS (a) Residual protective action Groundnut plants 10–15 cm in height are sprayed with a spray mixture (0.002%), prepared from a wettable powder formulation of the test compound, and infected 48 hours later with a conidia suspension of the fungus. The infected plants are incubated for 72 hours at about 21° C. and high humidity and then stood in a greenhouse until the typical leaf specks occur. Evaluation of the fungicidal action is made 12 days after infection and is based on the number and size of the specks.

(b) Systemic action

Groundnut plants 10–15 cm in height are sprayed with a spray mixture prepared from a wettable powder formulation of the test compound (0.06%, based on the volume of the soil). The treated plants are infected 48 hours later with a conidia suspension of the fungus and then incubated for 72 hours at about 21° C. and high humidity. The plants are then stood in a greenhouse and evaluation of fungus attack is made 11 days later. Compared with untreated and infected controls (number and size of the specks =100%), the plants treated with compounds of Tables 1 to 4 exhibit greatly reduced attack by Cercospora.

In the above tests, compounds 1.1, 1.3, 1.19, 1.22, 1.65 and others inhibit speck development almost completely (0 to 10%).

EXAMPLE B3: ACTION AGAINST ERYSIPHE GRAMINIS ON BARLEY (a) Residual protective action Barley plants about 8 cm in height are sprayed with a spray mixture (0.02%) prepared from the test compound formulated as a wettable powder. The treated plants are dusted with conidia of the fungus after 3–4 hours. The infected barley plants are then stood in a greenhouse at about 22° C. The extent of the infestation is evaluated after 10 days.

(b) Systemic action

Barley plants about 8 cm in height are treated with a spray mixture (0.006%, based on the volume of the soil) prepared from the test compound formulated as wettable powder. Care is taken that the spray mixture does not come in contact with the parts of the plants above the soil. The treated plants are infected 48 hours later with a conidia suspension of the fungus. The infected barley plants are then stood in a greenhouse at about 22° C. and evaluation of infestation is made after 10 days. Compounds of formula I and compounds of Tables 1 to 4 reduce fungus attack to less than 20%, whereas attack is 100% on untreated and infected control plants. Compounds 1.1, 1.3, 1.19, 1.22, 1.65 and others inhibit fungus attack completely (0–5%).

EXAMPLE B4: RESIDUAL-PROTECTIVE ACTION AGAINST VENTURIA INAEQUALIS ON APPLE SHOOTS

Apple cuttings with 10–20 cm long fresh shoots are sprayed with a spray mixture prepared from a wettable powder formulation of the test compound with a conidia suspension of the fungus. The plants are then incubated for 5 days at 90–100% relative humidity and stood in a greenhouse for a further 10 days at 20°–24° C. Scab infestation is evaluated 15 days after infection. Compounds 1.3, 1.19, 1.22 and others inhibit infestation to less than 10% and some (e.g. compound 1.3) inhibit infestation completely. Shoots on apple trees in field trials are protected to the same extent without being inhibited in their development.

EXAMPLE B5: ACTION AGAINST BOTYRITIS CINEREA ON BEANS

Residual protective action

Bean plants about 10 cm in height are sprayed with a spray mixture (0.02% concentration) prepared from the test compound formulated as wettable powder. After 48 hours, the treated plants are infected with a conidia suspension of the fungus. The infected plants are incubated for 3 days at 95–100% relative humidity and 21° C., and evaluation of the fungus attack is then made. Numerous compounds of Tables 1 to 4 inhibit fungus infection very strongly. For example, compounds 1.1, 1.3, 1.19, 1.22 and 1.65 are totally effective (0–5% attack) at a concentration of 0.02%.

EXAMPLE B6: ACTION AGAINST PIRICULARIA ORYZAE ON RICE

Residual-protective action

After being reared for 2 weeks, rice plants are sprayed with a spray mixture (0.02%) prepared from a wettable powder formulation of the test compound. The treated plants are infected 48 hours later with a conidia suspension of the fungus. Fungus attack is evaluated after incubation for 5 days at 95–100% relative humidity and 24° C. Compared with 100% attack on unprotected plants, compounds of Tables 1 to 4 inhibit fungus infestation significantly, e.g. compound 1.1 and others. Compound 1.51 inhibits fungus attack completely (0 to 3% attack) even when diluted to a concentration of 0.002%.

II. ACTION AGAINST INSECTS

EXAMPLE B7: ACTION AGAINST AEDES AEGYPTI

Active ingredient concentrations of 800 and 400 ppm respectively are obtained by pipetting a specific amount of a 0.1% solution in acetone of each compound to be tested onto the surface of 150 ml of water in each of a number of beakers. After the acetone has evaporated, 30 to 40 two-day-old larvae of Aedes aegypti are put into each of the beakers containing the test compound solution. Mortality counts are made after 1, 2 and 5 days.

In this test, compounds of Example 1 are very effective against Aedes aegypti. Very high mortality is achieved e.g. with compounds 1.19 and 1.22 (80–100%).

EXAMPLE B8: INSECTICIDAL STOMACH POISON ACTION

Potted cotton plants having a height of about 25 cm are sprayed with aqueous emulsions containing each compound to be tested in concentrations of 400 and 800 ppm. After the spray coating has dried, the cotton plants are populated with Spodoptera littoralis and Heliothis virescens larvae in the $L_3$-stage. The test is carried out at 24° C. and 60% relative humidity. The percentage mortality of of the test insects is determined after 120 hours.

Compounds of the formula I are very effective in this test. Compounds 1.19, 1.22 and others effect high mortality (75–100% kill) and are very well tolerated by plants.

EXAMPLE B9: INSECTICIDAL ACTION AGAINST APHIS CRACCIVORA

Bean plants which have grown roots are transplanted into pots containing 600 ccm of soil and then 50 ml of a solution containing 25 ppm, 5 ppm and 1 ppm of the compound to be tested are poured direct onto the soil.

After 24 hours the parts of the plants above the soil are populated with lice of the species Aphis craccivora and a plastic cylinder is then slipped over the plants to protect the lice from any possible contact with the test substance either direct or via the gas phase. A mortality count is made 48 hours after the start of the test. Two plants, each in a separate pot, are used for each test substance at its given concentration. The test is carried out at 25° C. and 70% relative humidity. Compounds of Tables 1 to 4 are very effective against Aphis craccivora. For example, compounds 1.10, 1.22 and others effect a mortality of 70 to 100%.

III. ACARICIDAL ACTION

EXAMPLE B10: ACTION AGAINST TETRANYCHUS URTICAE

Twelve hours before the test for acaricidal action, Phaseolus vulgaris plants are infected with an infested piece of leaf from a mass culture of Tetranychus urticae. The mobile stages which have migrated to the plants are sprayed from a chromatography atomiser with emulsions of the compound to be tested, such that the spray mixture does not run off. A count of living and dead organisms is made under a stereoscopic microscope after 2 and 7 days and the result is expressed in percent. During the test run the plants are stood in greenhouse compartments at 25° C.

In this test, compounds of Tables 1 to 4 have a good acaricidal action against Tetranychus urticae. Among others, compound 1.19 is fully effective against larvae, adults and eggs.

What is claimed is:

1. A phosphoric acid ester of the formula I

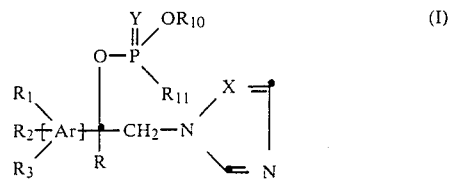

wherein

X is the bridge member —CH= or —N=,

Ar is a phenyl, diphenyl or naphthyl group, $R_1$, $R_2$ and $R_3$ are each independently hydrogen, nitro, halogen, $C_1$–$C_3$alkyl, $C_1$–$C_3$alkoxy or $C_1$–$C_3$haloalkyl, R is one of the groups —COOR$_4$, —COSR$_5$,

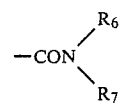

or —CN, $R_4$ is $C_2$–$C_{10}$alkenyl which is unsubstituted or substituted by halogen: $C_2$–$C_{10}$ alkynyl which is unsubstituted or substituted by halogen; or is a $C_3$–$C_8$cycloalkyl group or a phenyl group which is unsubstituted or substituted by halogen, $C_1$–$C_4$alkyl, $C_1$–$C_4$alkoxy, —CN or —CF$_3$; or is a $C_1$–$C_{12}$alkyl chain which from $C_2$alkyl may be interrupted by oxygen or sulfur and is unsubstituted or substituted by a member selected from the group consisting of halogen, phenyl, —COO—$C_1$–$C_4$alkyl, —CO—$C_1$–$C_4$alkyl, —CO—phenyl, an unsaturated or saturated 5- or 6-membered ring containing oxygen or sulfur as heteroatom, with each phenyl moiety being unsubstituted or substituted by one or more identical or different nitro groups, halogen atoms, or methyl groups $R_5$ is $C_1$–$C_{10}$alkyl, or is a phenyl or benzyl group, each unsubstituted or substituted by halogen, $C_1$–$C_4$alkyl, $C_1$–$C_4$alkoxy, —CN or —CF$_3$, $R_6$ and $R_7$ are each independently hydrogen, $C_1$–$C_6$alkyl, $C_3$–$C_7$cycloalkyl, or a phenyl or benzyl group in each of which the aromatic ring is unsubstituted or substituted by halogen, $C_1$–$C_4$-alkyl, $C_1$–$C_4$alkoxy, —CN or —CF$_3$, or one of $R_6$ and $R_7$ is also the —N($R_8$)($R_9$) group, or both taken together form a 5- or 6-membered saturated or unsaturated heterocyclic ring which may additionally contain 1 or 2 further N-atoms, $R_8$ and $R_9$ are each independently hydrogen, $C_1$–$C_4$alkyl or a phenyl radical which is unsubstituted or substituted by halogen, $C_1$–$C_4$alkyl, —CN or —CF$_3$, $R_{10}$ is $C_1$–$C_{12}$alkyl, and $R_{11}$ is —YR$_{12}$, $C_1$–$C_{12}$alkyl or phenyl, $R_{12}$ is $C_1$–$C_{12}$alkyl and Y is oxygen or sulfur, or an acid addition salt, quaternary azolium or ammonium salt, or a metal complex thereof, 2. A compound according to claim 1, of the formula I*

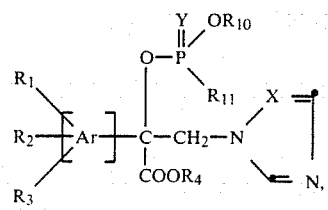 (I*)

wherein
- $R_4$ is $C_1$–$C_4$alkyl, phenyl, benzyl or phenyl or benzyl, each substituted by one or more nitro groups, halogen atoms and/or methyl groups,
- $R_{10}$ is $C_1$–$C_6$alkyl,
- $R_{11}$ is —$YR_{12}$, $C_1$–$C_6$alkyl or phenyl, and
- $R_{12}$ is $C_1$–$C_6$alkyl, or an agriculturally suitable acid addition salt, quaternary azolium or ammonium salt, or a metal complex thereof.

3. A compound of the formula I according to claim 1, wherein Ar is a phenyl group; $R_1$ in the orthoposition is hydrogen, nitro, halogen, $C_1$–$C_3$alkyl, $C_1$–$C_3$alkoxy, or $C_1$–$C_3$haloalkyl; $R_2$ in the para-position is hydrogen, nitro, halogen, $C_1$–$C_3$alkyl, $C_1$–$C_3$alkoxy or $C_1$–$C_3$-haloalkyl; $R_3$ is hydrogen, methyl or halogen; R is a group —$COOR_4$, —$COSR_5$,

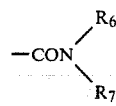

or —CN; $R_4$ is $C_1$–$C_4$alkyl, phenyl, benzyl, or phenyl or benzyl, each substituted by one or more nitro groups, halogen atoms and/or methyl groups; $R_5$ is $C_1$–$C_{10}$alkyl, or phenyl or benzyl, each unsubstituted or substituted by halogen, $C_1$–$C_4$alkyl, $C_1$–$C_4$alkoxy, —CN or —$CF_3$; each of $R_6$ and $R_7$ independently is hydrogen, $C_1$–$C_3$alkyl, $C_3$–$C_7$cycloalkyl, phenyl or benzyl; $R_{10}$ is $C_1$–$C_4$alkyl; $R_{11}$ is —$YR_{12}$, $C_1$–$C_4$alkyl or phenyl; and $R_{12}$ is $C_1$–$C_4$alkyl; or an acid addition salt, quaternary azolium or ammonium salt, or a metal complex thereof.

4. A compound of the formula I according to claim 3, wherein X is the bridge member —N=; the grouping

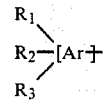

is a phenyl group which is substituted in the ortho- and/or para-position by nitro, fluorine, chlorine, bromine, methyl, methoxy and/or $CF_3$; R is the —$COOR_4$ group; $R_4$ is $C_1$–$C_4$alkyl, phenyl, obenzyl, or phenyl or benzyl, each substituted by nitro, chlorine, bromine, fluorine and/or methyl; $R_{10}$ is $C_1$–$C_4$alkyl; $R_{11}$ is —$YR_{12}$, $C_1$–$C_4$alkyl or phenyl; $R_{12}$ is $C_1$–$C_4$-alkyl; or an acid addition salt, quaternary azolium or ammonium salt, or a metal complex thereof.

5. The compound of the formula

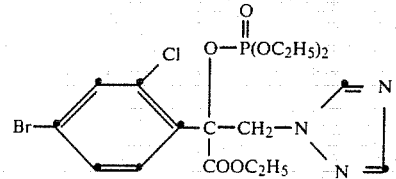

according to claim 4.

6. The compound of the formula

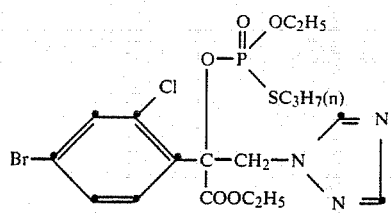

according to claim 4.

7. The compound of the formula

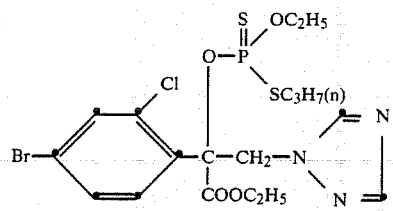

according to claim 4.

8. The compound of the formula

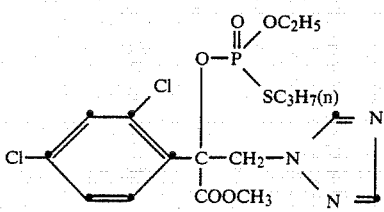

according to claim 4.

9. A metal complex of the formula I according to claim 1 with copper, zinc, manganese or tin.

10. A pesticidal composition for controlling or preventing infestation of plants by fungi, bacteria, insects or acarides, which composition contains a pesticidally effective amount of at least one compound of the formula I as claimed in claim 1, together with suitable carriers therefor.

11. A method of controlling phytophatogenic fungi, insects or acarina or of protecting cultivated plants from attack by such pests, which comprises applying to said plants or to the locus thereof a pesticidally effective amount of a compound of the formula I as claimed in claim 1.

* * * * *